(12) United States Patent
Nakai

(10) Patent No.: US 6,231,703 B1
(45) Date of Patent: *May 15, 2001

(54) ELECTROMAGNETIC WAVE SHIELD MAGNET, METHOD FOR MAKING THE MAGNET, AND ELECTROMAGNETIC WAVE SHIELD ARTICLE

(75) Inventor: Yoshinaga Nakai, Takefu (JP)

(73) Assignee: Junrou Suehiro (JP); a part interest ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/040,845

(22) Filed: Mar. 18, 1998

(30) Foreign Application Priority Data

| Mar. 19, 1997 | (JP) | ................................................. 9-85875 |
| Apr. 2, 1997 | (JP) | ................................................. 9-97915 |
| Apr. 4, 1997 | (JP) | ................................................. 9-102780 |
| Sep. 21, 1997 | (JP) | ................................................. 9-275280 |

(51) Int. Cl.[7] ............................................. B32B 31/00

(52) U.S. Cl. ............................ 156/60; 29/458; 427/127

(58) Field of Search ............................ 335/322, 306; 264/171.28; 156/60, 278; 427/127; 29/458

(56) References Cited

U.S. PATENT DOCUMENTS

| 4,285,819 | * | 8/1981 | Yen et al. ............................... 210/679 |
| 4,612,247 | * | 9/1986 | Walsh et al. ....................... 210/688 X |
| 4,681,712 | * | 7/1987 | Sakakibara et al. ............ 264/171.28 |
| 4,798,694 | * | 1/1989 | Sugata et al. .................... 264/171.28 |
| 4,868,106 | * | 9/1989 | Ito et al. .................................. 435/7 |
| 4,935,147 | * | 6/1990 | Ullman et al. ........................ 210/695 |
| 5,076,950 | * | 12/1991 | Ullman et al. ..................... 252/62.51 |
| 5,279,936 | * | 1/1994 | Vorpahl ..................................... 435/6 |
| 5,283,064 | * | 2/1994 | Suzuki et al. ......................... 424/451 |
| 5,319,397 | * | 6/1994 | Ryden ..................................... 351/62 |
| 5,536,644 | * | 7/1996 | Ullman et al. ...................... 435/7.25 |
| 5,642,177 | * | 6/1997 | Nishioka ................................ 351/47 |
| 5,770,388 | * | 6/1998 | Vorpahl ................................ 435/7.25 |

\* cited by examiner

Primary Examiner—Jeff H. Aftergut
(74) Attorney, Agent, or Firm—Bierman, Muserlian and Lucas

(57) ABSTRACT

The electromagnetic wave shield magnet is used on conductive articles such as eyeglasses and earrings to block or reduce the effect of stray electromagnetic waves on the user. Additionally, the article can have a conductive coating and an insulating coating to increase the reduction of the stray electromagnetic waves. The magnet is made by treating a base magnet with an alkali aqueous solution which contains chitosan. The article can also be made with just the conductive coating or with the conductive coating and the insulating coating.

8 Claims, 13 Drawing Sheets

```
┌─────────────────────────────────────┐
│    Conductive pigment e.t.c. were   │
│  mixed with blended liquid of silicon│
│    resin and hardener on the market.│
└─────────────────────────────────────┘
                  │
┌─────────────────────────────────────┐
│   Kerosene and glycol were added to the│
│   mixture and heated to about 60 - 70°C.│
└─────────────────────────────────────┘
                  │
┌─────────────────────────────────────┐
│   The mixture was fused about 40 min at│
│     a temperature of about 60 - 70°C.│
└─────────────────────────────────────┘
                  │
┌─────────────────────────────────────┐
│    Fused conductive coating was heated│
│ to about 120°C - 160°C and sprayed or coated│
│   on washed lens frames e.t.c. with brush.│
└─────────────────────────────────────┘
```

ELECTROMAGNETIC WAVE SHIELD MAGNET, METHOD FOR MAKING THE MAGNET, AND ELECTROMAGNETIC WAVE SHIELD ARTICLE

BACKGROUND OF THE INVENTION

1. Field of the Invention

This invention relates to an electromagnetic wave shield magnet, a method for making the magnet and an article of manufacture which acts as a shield from electromagnetic waves. The articles of manufacture made in accordance with the present invention include eyeglasses, masks that protect the head and face of the wearer, and earrings. The purpose of the article of the present invention is to protect the head area of a user and inhibit the harmful effects caused by stray electromagnetic waves generated at home and in the work place.

2. Prior Art

Apparatus such as personal computers, word processors, portable telephones, microwave ovens and the like generate electromagnetic waves which can be harmful to the user. Personal computers, word processors, and the like typically employ cathode ray tubes which operate by means of an electronic gun or electronic beam source that projects an electronic beam onto a luminant and projects a picture. These electronic guns operate at a high voltage and emit electromagnetic waves. Electromagnetic waves are also generated by various kinds of other electronic apparatus such as portable telephones, microwave ovens, car engines, electric shavers, electric dryers and the like.

It is generally believed that stray electromagnetic waves from such apparatuses are harmful to the user. It has been reported that the surface of the cornea of mice and guinea pigs has been injured after long exposure to electromagnetic waves. It is also thought that electromagnetic waves can cause cataracts, brain tumors, and nerve lesions. Such lesions occur on the optic nerves and the periphery nerves such as the auditory nerves and the central nerves. The full effect on a human from stray electromagnetic waves has yet to be fully determined.

It is known that stray electromagnetic waves have a detrimental effect on the measurement precision of medical and scientific apparatus.

Since the intensity of electromagnetic waves is inversely proportional to the square of the distance, it is preferred to stay away from devices that generate electromagnetic waves. Keeping a safe distance, however, is hard or impossible to do with personal computers, portable telephones, microwave ovens and the like. Ceramic powders and ferrite have been used in the past as a shield for medical and scientific apparatus from electromagnetic waves. Typically, the powders and ferrite are applied to the exterior of the device to cut down or eliminate the influence of the waves. These materials have also been applied to the exterior of these devices that generate the electromagnetic waves, such as the exterior shell of the microwave oven to reduce or eliminate the stray electromagnetic waves.

SUMMARY OF THE INVENTION

An electromagnetic wave shield magnet, a method for making the magnet, and an article of manufacture which acts as a shield against harmful electromagnetic waves has now been discovered.

The articles of manufacture which are made in accordance with the present invention include eyeglasses, masks for protecting the head area of the user, aprons worn in the workplace and at home, earrings, and the shell which surrounds medical and scientific devices which are in need of protection from the stray electromagnetic waves.

Broadly, in accordance with the present invention, an electromagnetic wave shield magnet comprises a base magnet which has been treated with an alkali aqueous solution containing chitosan as an essential ingredient therein. The treatment causes the base magnet to become impregnated with the solution and to become negatively ionized after the treatment.

The article of manufacture of the present invention comprises a conductive article on which an electromagnetic wave shield magnet of the present invention has been affixed, or on which a conductive coating and/or an insulating coating has been applied. Preferably, the article made in accordance with the present invention having the electromagnetic wave shield magnet of the present invention affixed thereto also has a conductive coating and, more preferably, an insulating coating thereon. The conductive coating and the insulating coating used in the present invention are liquids which dry and adhere to the conductive article. The conductive coating comprises a conductive pigment, a liquid silicone and hardeners. The insulating coating comprises an insulating pigment, a polyurethane and hardeners.

BRIEF DESCRIPTION OF THE DRAWINGS

These and other aspects of the present invention may be more fully understood by reference to one or more of the following drawings wherein like reference numerals have been used for like characteristics in the drawings.

FIG. 16 illustrates a process for making the conductive coating and coating a lens in accordance with the present invention;

DETAILED DESCRIPTION OF THE INVENTION

Figure 1:
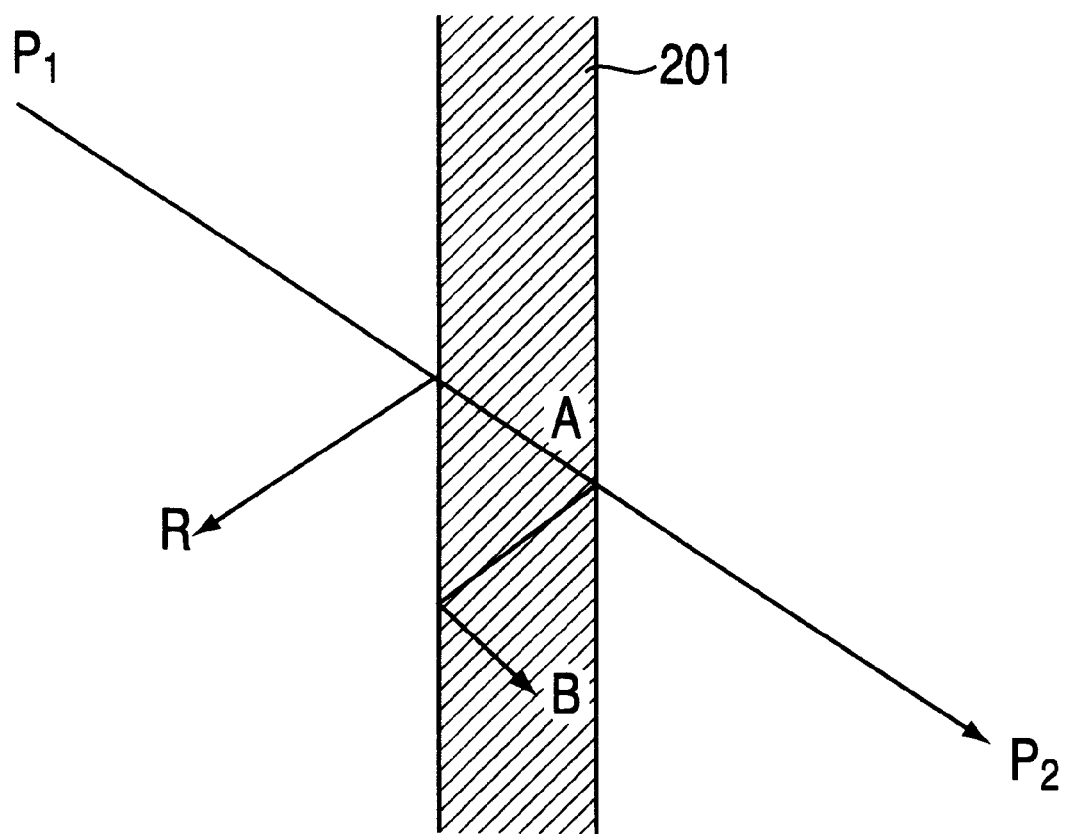
FIG. 1 illustrates a schematic diagram of an electromagnetic wave shield mechanism according to the present invention.

FIG. 1 illustrates the electromagnetic wave shield mechanism according to the present invention. Incident electromagnetic wave P1 contacts electromagnetic wave shield material 201 and passes through and out of electromagnetic wave shield material 201 as transmitted electromagnetic wave P2. Certain losses occur in this transition. These losses are reflective loss R, absorption loss A and multiple loss B. Reflective loss R comes from the loss when incidental electromagnetic wave P1 is reflected in part from the surface of the electromagnetic wave shield material 201. Absorption loss A comes from the loss when incident electromagnetic wave P1 generates induced current inside material 201 which is then absorbed in material 201. Multiple loss B occurs from reflective loss and absorption loss inside material 201. Multiple loss B is small compared to reflective loss R and absorption loss A. The shielding effect of material 201 is defined as:

$$SE(dB)=R+A+B$$

Figure 2:
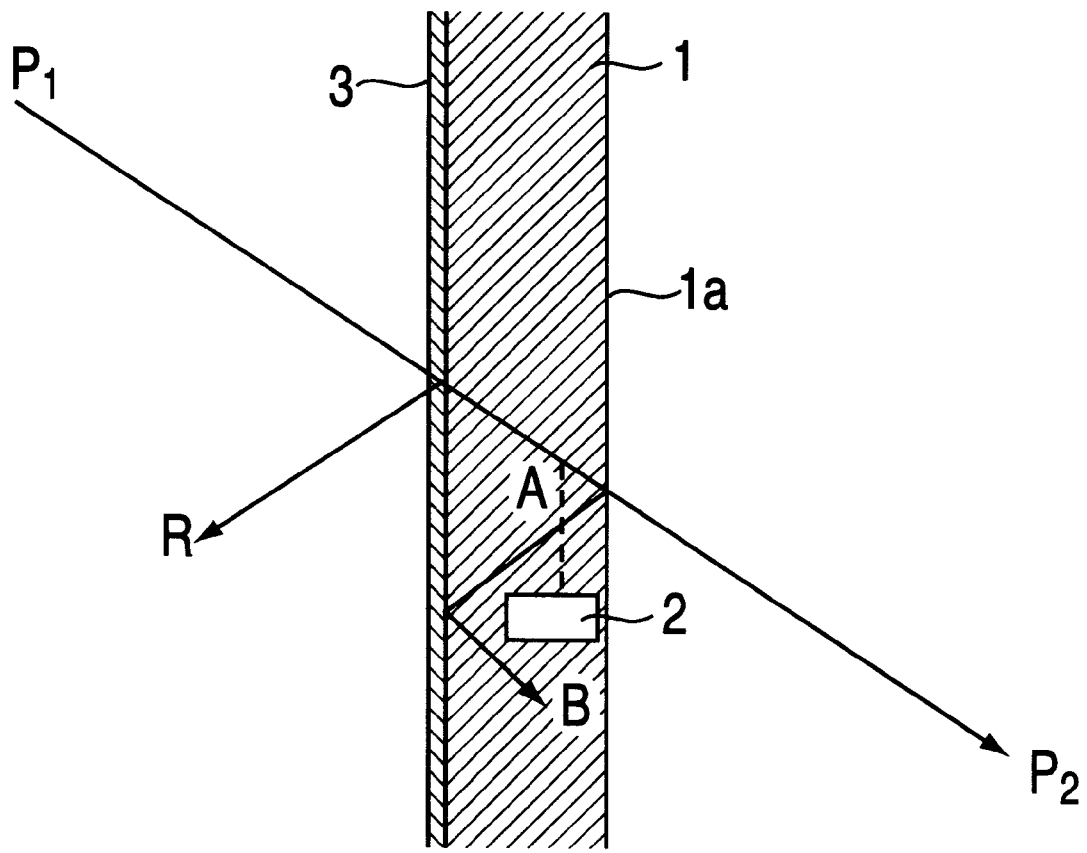
FIG. 2 illustrates a schematic diagram of an electromagnetic wave shield mechanism wherein an electromagnetic wave shield magnet and a conductive coating are employed according to the present invention.

FIG. 2 illustrates conductive article 1 with a magnet 2 which has been made in accordance with the present invention. Applied to article 1 is conductive coating 3, also made in accordance with the present invention.

When a conductive coating and an insulating coating are employed, incident electromagnetic waves P1, the absorption and reflective values R and A are increased and the transmitted electromagnetic wave P2 is decreased in magnitude. There is a correlation between the surface resistance and the shield effect. Surface resistance is a value of specific resistance divided by thickness. The lower the surface resistance, the higher the shield effect.

Inductive electric current B of incident electromagnetic wave P1 is absorbed by magnet 2 as shown in FIG. 2. Additionally, inductive electric current B is increased by the existence of magnet 2 in article 1. Incident electromagnetic wave P1 is reflected and absorbed in conductive coating 3, therefore, reflective loss R, absorption loss A and multiple loss B are increased, thereby decreasing the intensity of transmitted electromagnetic wave P2. Additionally, when article 1 has an insulating coating on its reverse side, side 1a, or between conductive coating 3 and article 1, absorption of the electromagnetic wave is increased.

The resistivity and the decay rate of electromagnetic waves for an article made in accordance with the present invention employing the magnet of the present invention were tested and reported to be as follows:

surface resistivity (the value by applying 500 voltage at intervals of 2.5 cm on an article made in accordance with the present invention having a 25 micron thick conductive coating measured by JIS:Japanese Industrial Standard method) was 2 ohms/cm$^2$ and less;

volume resistivity corresponding to this surface resistivity was measured to be $5.0 \times 1/10^3$ ohms.cm (in conformity with JIS-K6911);

electromagnetic wave decay rate (the value by applying 30–1000 megahertz of electromagnetic waves to an article made in accordance with the present invention having a 25 micron thick conductive coating and insulating coating each) was measured to be 40–65 db.

Figure 3:
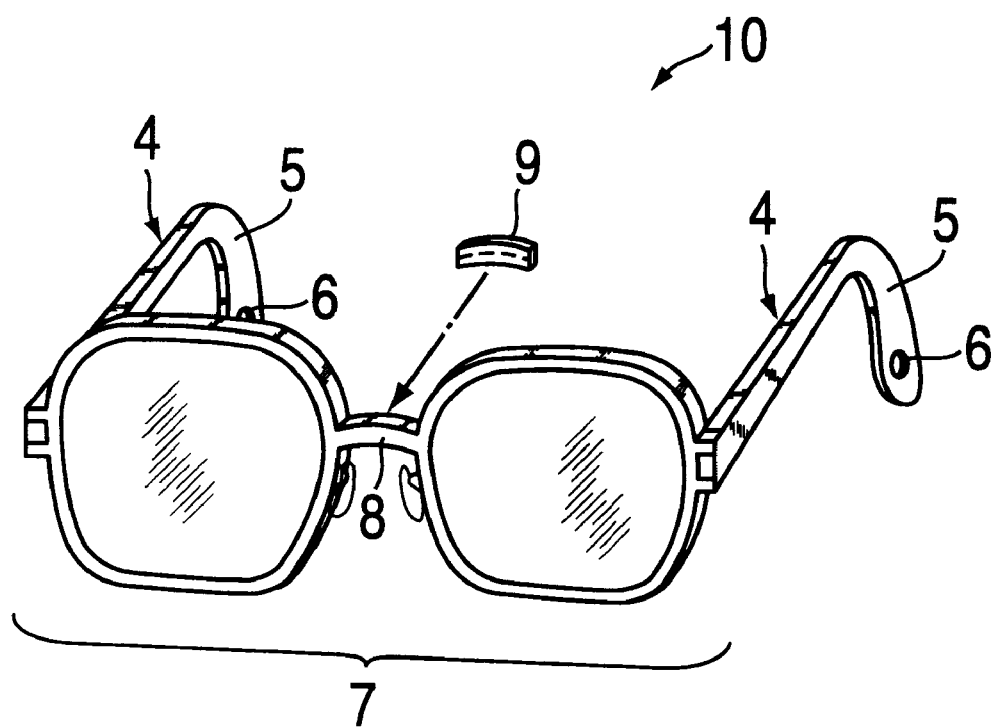
FIG. 3 illustrates a pair of eyeglasses with electromagnetic wave shield magnets affixed thereto.

FIG. 3 illustrates eyeglasses 10 having temples 4, ear pieces 5, two electromagnetic wave shield magnets 6 set in ear pieces 5, lens frame 7, and bridge 8. Affixed to bridge 8 is electromagnetic wave shield magnet 9 which is shaped like bridge 8. Eyeglasses 10 can be made of any material such as plastic or metal which conducts electromagnetic waves therethrough.

Electromagnetic wave shield magnets 6 are about 2 to 3 mm in diameter, shaped like cylinders and set in holes which are formed in ear pieces 5. Magnets 6 can take on any shape such as cylinders, cones or the bridge of the eyeglasses as magnet 9. Magnet 9 is affixed to bridge 8 by means of a glue such as an epoxy. Any means of affixing magnets 6 and 9 to eyeglasses 10 can be employed.

In order to make an electromagnetic wave shield magnet in accordance with the present invention, a base magnet is treated with an alkali aqueous solution containing chitosan as an essential ingredient therein; and the treated magnet is recovered.

Suitable base magnets for use in the present invention include ferrite magnets, plastic bonded magnets, and rare earth magnets.

Suitable alkalis for use in the present invention include sodium hydroxide (NaOH), potassium hydroxide (KOH) and calcium hydroxide (Ca(OH)$_2$). The pH of the solution is preferably about 12 to about 14 and more preferably about 13 to 14. Good results have been obtained at a pH of about 14.

Chitosan is a beta(1–4)polyglucosamine which is a de-acetylide of chitin obtained from the extract of Crustacea and certain algae. Typically, it has a formula $(C_6H_{11}NO_4)n$. Chitan obtained from Crustacea such as crab, prawns, etc., is suitable for the present invention. A value for n of about 5 to about 7 is suitable. Any suitable source of chitosan can be used. The amount of chitosan used in the solution is about 10 g to about 50 g and, more preferably, about 20 g to about 40 g.

The solution also contains an enzyme that degraded the chitosan. Suitable enzymes include adenosine triphosphatase, endopeptidase, and deoxyribonuclease. The amount of enzyme used in the solution is about 5 g to about 25 g and, more preferably, about 10 g to about 20 g.

It has been found that the treatment impregnates the base magnet with the solution and the base magnet becomes negatively ionized.

Figure 4:
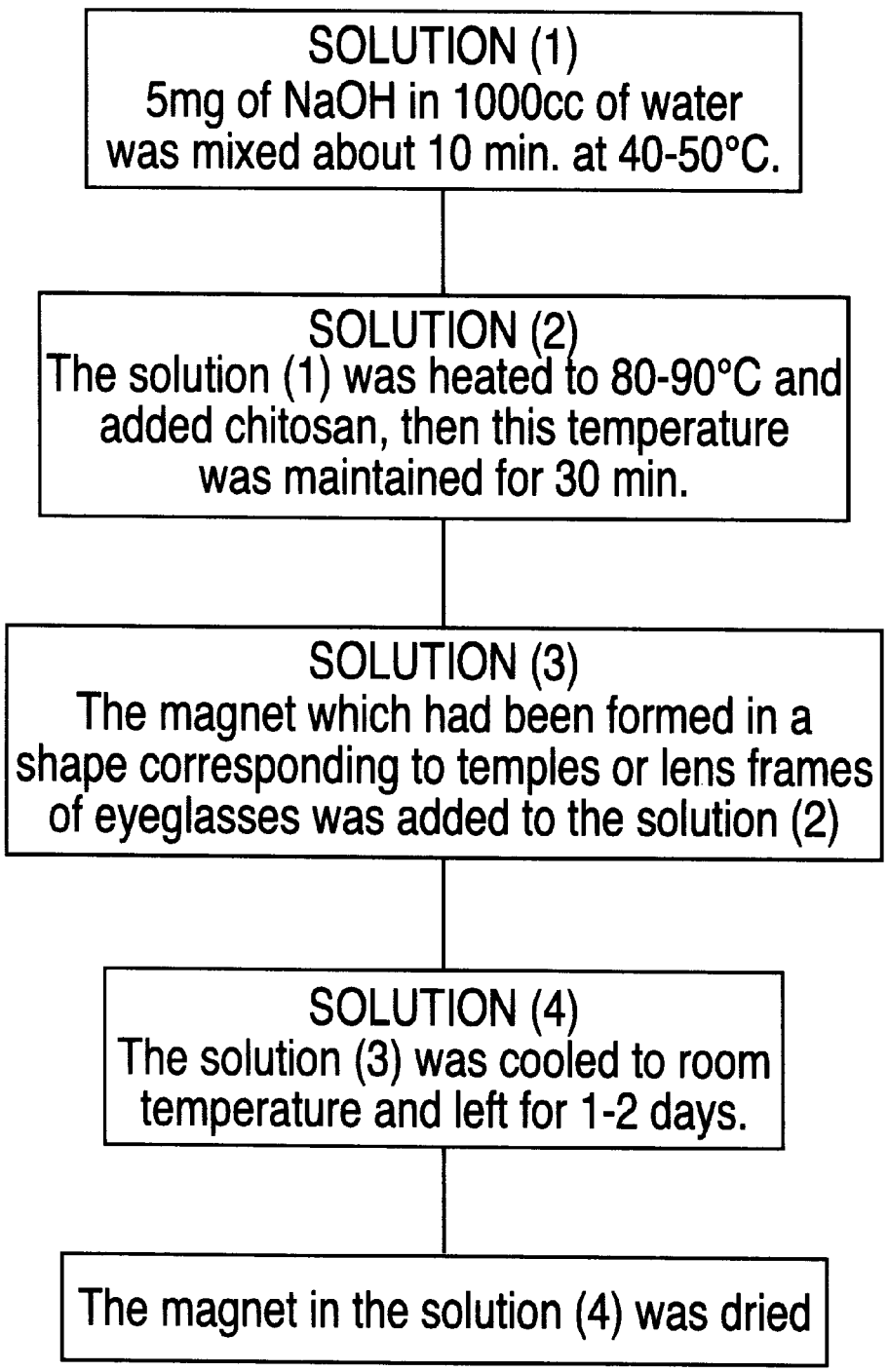
FIG. 4 illustrates a preferred embodiment of the process for preparing an electromagnetic wave shield magnet.
Figure 5:
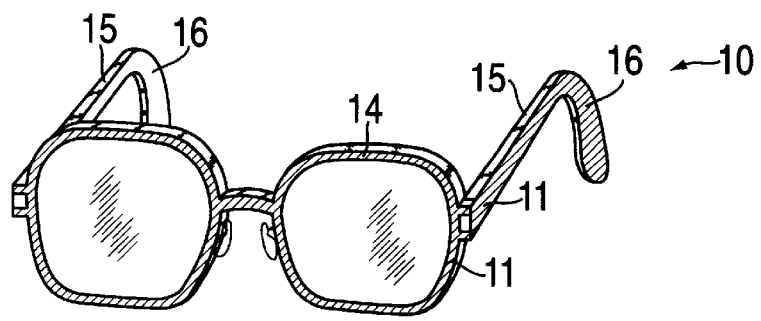
FIG. 5 illustrates a pair of eyeglasses having a conductive coating on the surface of the lens frame and temples.

FIG. 4 illustrates a preferred process for making the electromagnetic wave shield magnet in accordance with the present invention. First an alkali aqueous solution was prepared by mixing 5 mg of NaOH in 1000 cc of water at a temperature of about 40 to about 50° C. for a period of about 10 minutes. Second, the solution was heated to about 80° C. to about 90° C., and the enzyme and chitosan were added to the heated solution. The solution was maintained at that temperature for a period of about 30 minutes to allow for degradation of the chitosan. Third, the base magnet was added to the solution. Fourth, the solution was allowed to cool to room temperature and allowed to stand at room temperature for about one (1) to two (2) days. Fifth, the treated base magnet was removed from the solution and dried.

FIGS. 5 through 15 illustrate an electromagnetic wave shield article of the present invention comprising a conductive article onto which a conductive coating and/or an electromagnetic wave shield magnet made in accordance with the present invention has been applied. Preferably, the electromagnetic wave shield article comprises both a conductive coating and the magnet, and, more preferably, further comprises an insulating coating.

In FIGS. 5–10, eyeglasses 10 has conductive coating 11 applied to predetermined parts thereof. Insulating coating 12 has also been applied to predetermined parts of eyeglasses 10. Transparent conductive coating 13 has been applied to the surface of the lens of eyeglasses 10 and acts like conductive coating 11 except for the fact that it is transparent. Also illustrated are lens frame 14, temples 15, parts of temples 16 which are worn on the ears, ends 17 which are part of temples 15 and are worn on the ears, keeping paper battery 18, and hearing aid 19 set on the ends 17.

Figure 11A:
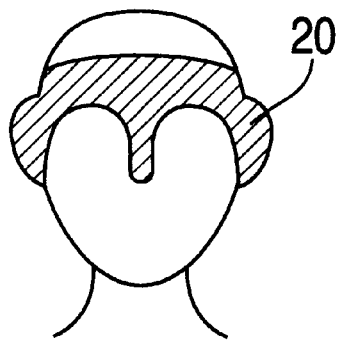
FIGS. 11(a), 11(b) and 11(c) illustrate a front, side and top view, respectively, of an electromagnetic wave shield mask having a conductive coating on the surface, and an insulating coating on the reverse side.
Figure 11B:
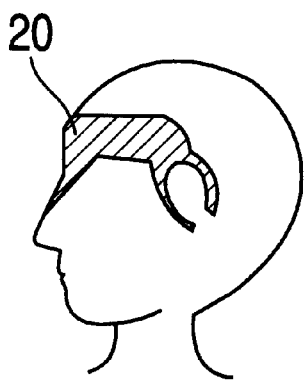
Figure 11C:
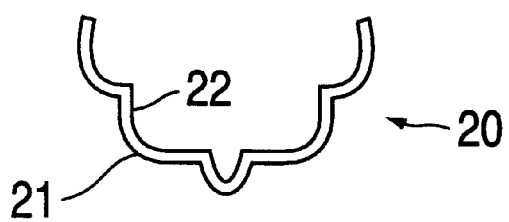

FIGS. 11(a), 11(b) and 11(c) show mask 20, electromagnetic wave shield conductive coating 21 which coats the surface of mask 20, and electromagnetic wave shield insulating coating 22 which is coated on the reverse side of mask 20. Where mask 20 has a lens to protect the eyes of the user, a transparent coating is preferably applied to the lens.

In FIGS. 12–15 earrings 101 have conductive coating 102 applied to predetermined parts thereof. Preferably, insulating coating 103 is also applied to predetermined parts of earrings 101. Main part 110 of earrings 101 has branches 111, twigs 112 and ends 113. Magnets 114, made in accordance with the present invention, are attached to earrings 101 by chains 115. Clips for fitting earrings 101 to a user's ear are fixed on the reverse side of main part 110.

Figure 9:
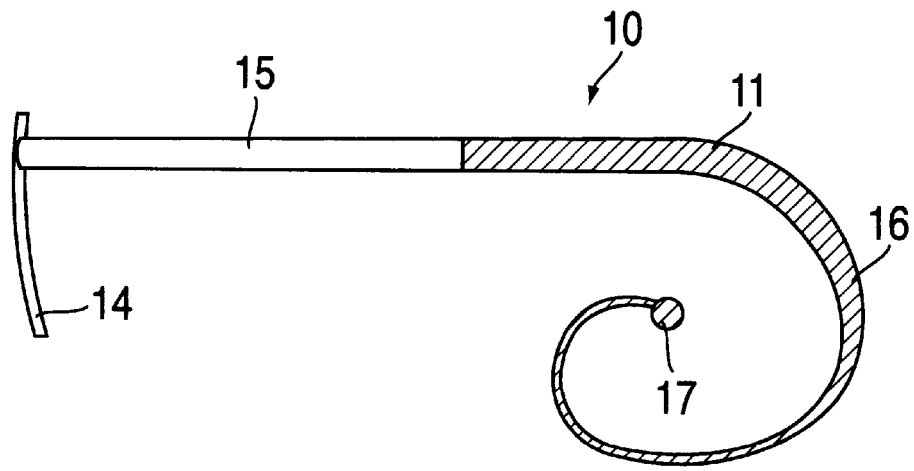
FIG. 9 illustrates a pair of eyeglasses having a conductive coating on all parts of the temples which are worn on the ears.
Figure 10:
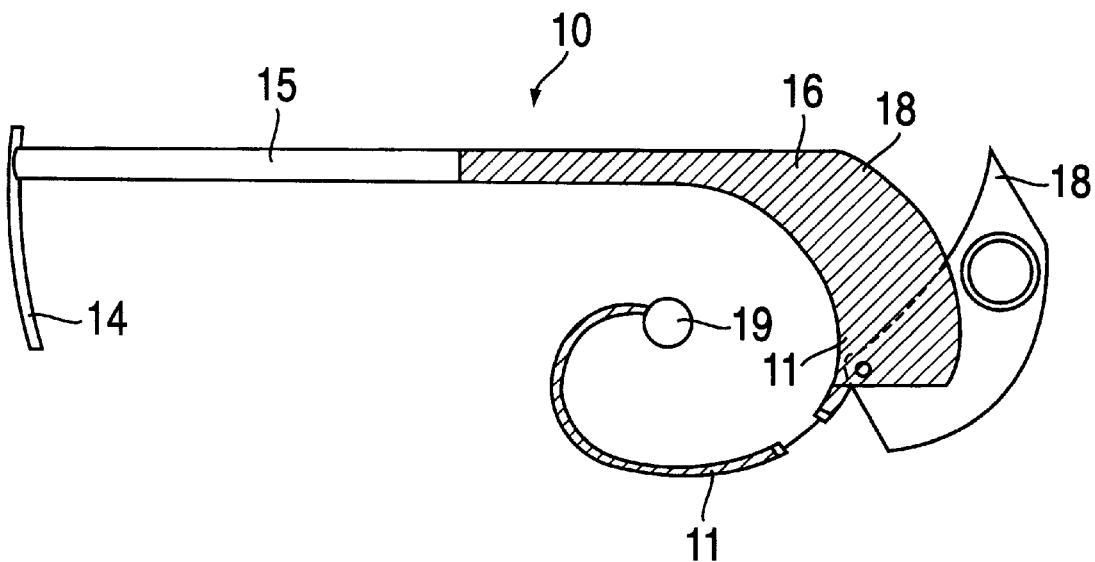
FIG. 10 illustrates a pair of eyeglasses having a conductive coating on the surface of a portion of the keeping paper battery.

In FIGS. 9 and 10, the parts of temples 16 which are worn on the ears is curved to allow ends 17 to reach the user's external auditory canal when eyeglasses 10 are worn. As shown, keeping paper battery 18 can be pivoted. Also, paper battery 18 and speaker for hearing aid 19 are, for example, connected by internal wiring in the pipe-shaped parts of the eyeglasses which are worn on the ears.

It will be understood, although not illustrated, that the tip of receiving circuit may be set on the portion for keeping paper battery 18 and that the speaker for hearing aid 19 may be set on ends 17 of parts 16 of eyeglasses which are worn on the ears.

Electromagnetic waves generated from personal computers, portable telephones, microwave ovens, etc. are absorbed into and/or reflected by conductive coating 11, 13, 21 and insulating coating 12, 22 which are coated on the article at predetermined places. In this manner, electromagnetic wave energy is reduced to the user and the article functions as a shield against stray electromagnetic waves.

Figure 6:
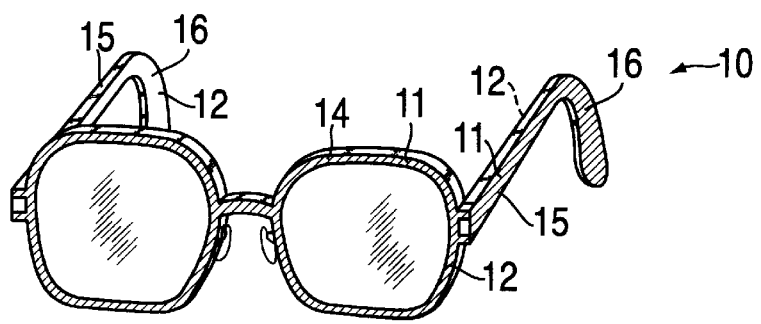
FIG. 6 illustrates a pair of eyeglasses having a conductive coating on the upper part of the lens frame, the surface of the temples and an insulating coating on the lower part of the lens frame and the reverse side of the temples.
Figure 7:
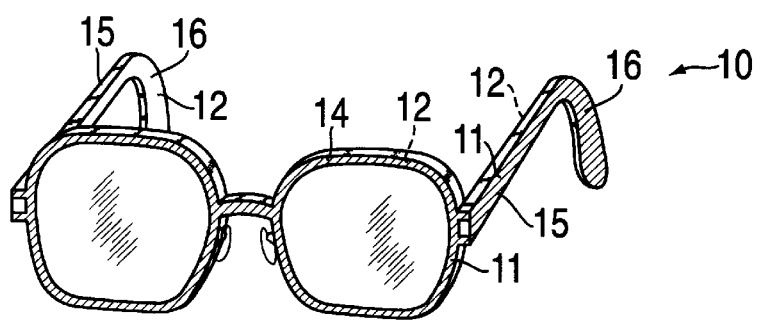
FIG. 7 illustrates a pair of eyeglasses having a conductive coating on the surface of the lens frame and the temples, and an insulating coating on the reverse side of the lens frame and the temples.

In the case of eyeglasses illustrated in FIGS. 6 and 7, for example,
- electromagnetic waves were absorbed into and/or reflected by conductive coating 11 which was coated on the surface of lens frame 14 and temples 15;
- electromagnetic waves (which was transmitted through conductive coating 11) were absorbed into insulating coating 12 which was coated on the reverse side of lens frame 14 and temples 15. By causing dielectric polarization, the insulating coating absorbs electromagnetic waves.

In the case of eyeglasses 10 in FIG. 9, ends 17 of parts 16 of eyeglasses 10 which are worn on the ears and which reach the external auditory canal, absorb and reflect electromagnetic waves by means of conductive coating 11. The same was true for eyeglasses 10 in FIG.10.

Figure 8:
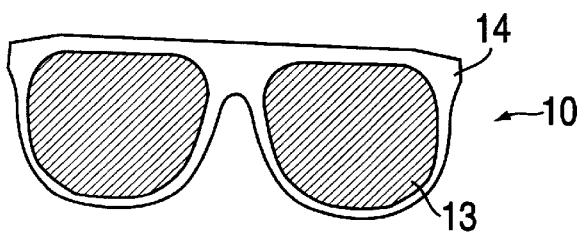
FIG. 8 illustrates a pair of eyeglasses having a transparent conductive coating on the surface of the lens.

FIG. 11(a) shows a front view of mask 20, FIG. 11(b) shows a side view of mask 20, and FIG. 11(c) shows a top view of mask 20. Mask 20 is shaped so as to cover the forehead of the user and prevent the bad influences of stray electromagnetic waves to the head of the user. As shown in FIG. 11(a), mask 20 does not cover the eyes, however, it can be designed to cover eyes. In this case, a transparent conductive coating as shown in FIG. 8 is coated on the parts which correspond to the lens for the eyes.

Stray electromagnetic waves generated from electric apparatus are blocked by conductive coating 21 which is coated on the surface of mask 20 and electromagnetic waves which are transmitted through this conductive coating 21 are absorbed into insulating coating 22.

Conductive coating 11, 21 and insulating coating 12, 22 can be coated on some or all of parts of the eyeglasses or the masks. For example, the conductive coating can be coated on ends 17 of the eyeglasses as shown in FIGS. 5–8; or, as shown in FIGS. 9 and 10, the conductive coating can be coated on the whole surface of temples 15.

Further, each part coated with the conductive coating and the insulating coating is not restrictive according to disclosure in FIGS. 5–11. For example,
- conductive coating 11 can be coated on the reverse side of lens frame 14, temples 15;
- in the case of the eyeglasses illustrated in FIG. 8, insulating coating 12 can be coated on the reverse side of the lens or, conductive coating 11 can be coated on lens frame 14;
- in the case of the eyeglasses illustrated in FIGS. 9 and 10, conductive coating 11 and insulating coating 12 can be coated on lens frame 14, the lens and other parts of ends 17 which are worn on the ears selectively.

Figure 12:
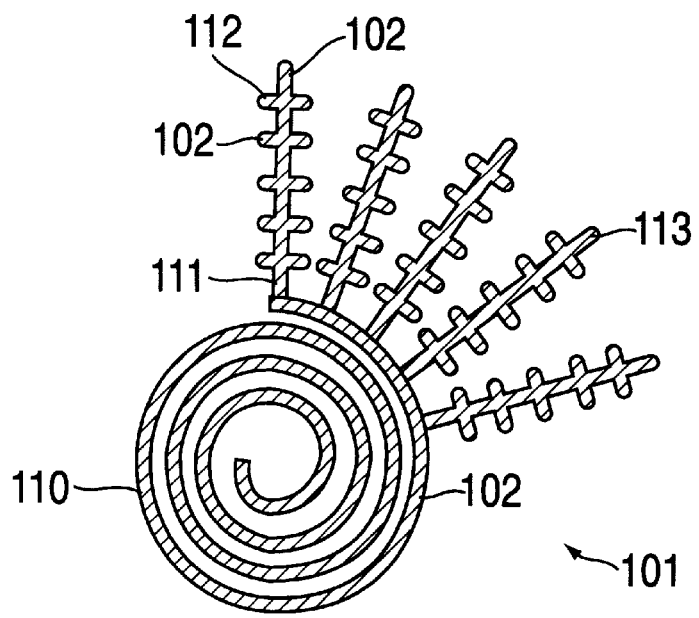
FIG. 12 illustrates the surface of an earring having a main part in a coil-shaped of left-handed turning, and forms five branches radiating in an outward direction.

In FIG. 12, earrings 101 has branches 111 with five twigs 112 and ends 113 of branches 111 are round-shaped in consideration of safety. Conductive coating 102 is coated on each of these parts.

Electromagnetic waves generated from portable telephones are reflected by and/or absorbed into conductive coating 102 which is coated on main part 110, branches 111, and twigs 112. As a result, electromagnetic waves which have bad influence on human body are reduced.

Figure 13:
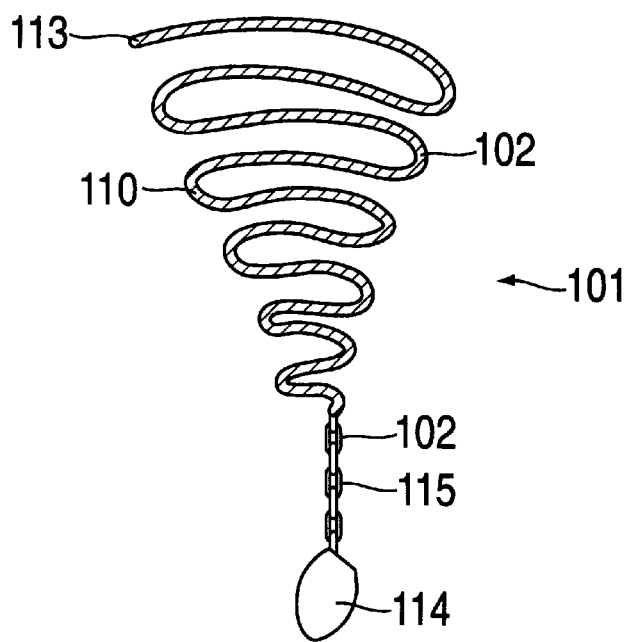
FIG. 13 illustrates the surface of a wave-shaped earring with a magnet in accordance with the present invention.

In FIG. 13, main part 110 of earrings 101 is wave-shaped and below it, magnet 114 is attached by chain 115. Conductive coating 102 is coated on main part 110 and end 113 is round-shaped in consideration of safety.

Electromagnetic waves are reflected by and/or absorbed into conductive coating 102 which is coated in main part 110, absorbed into magnet 114.

Figure 14A:
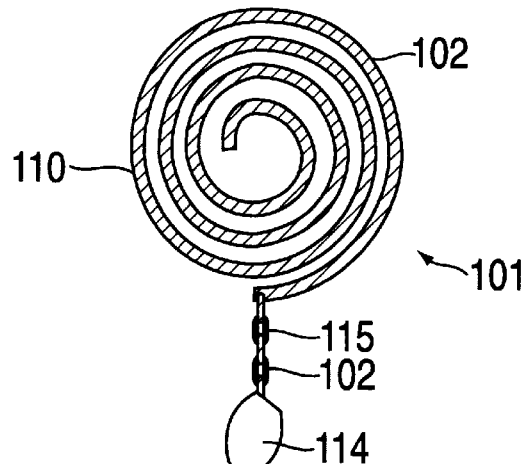
FIGS. 14(a), 14(b) and 14(c) illustrate other preferred embodiments of earrings in accordance with the present invention.
Figure 14B:
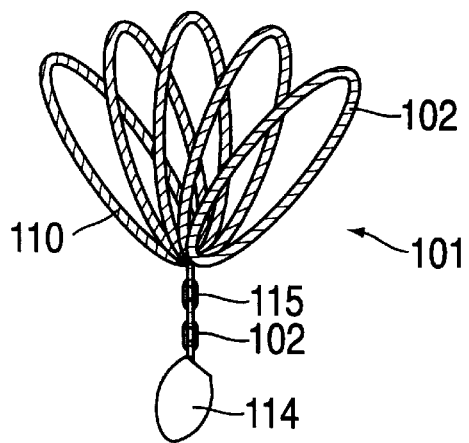
Figure 14C:
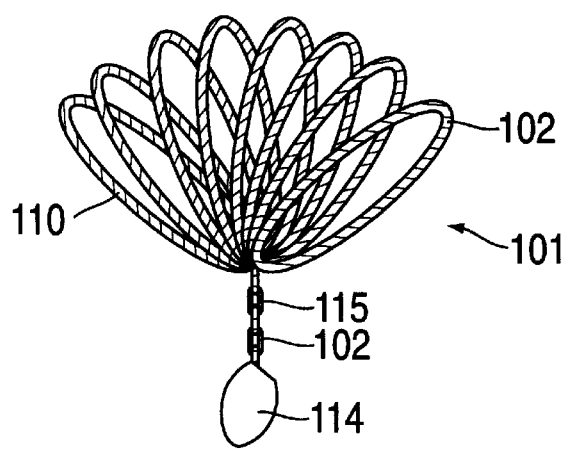

FIG. 14(a) shows coil-shaped, right-handed turn earrings 101 with magnet 114. FIG. 14(b) and 14(c) show earrings 101 formed with a plurality of rings. These earrings are formed so as to block electromagnetic waves as widely as possible. Electromagnetic waves are blocked by a conductive coating which is coated on main parts 110 and by magnet 114 which is attached to the earrings by chain 115.

Figure 15:
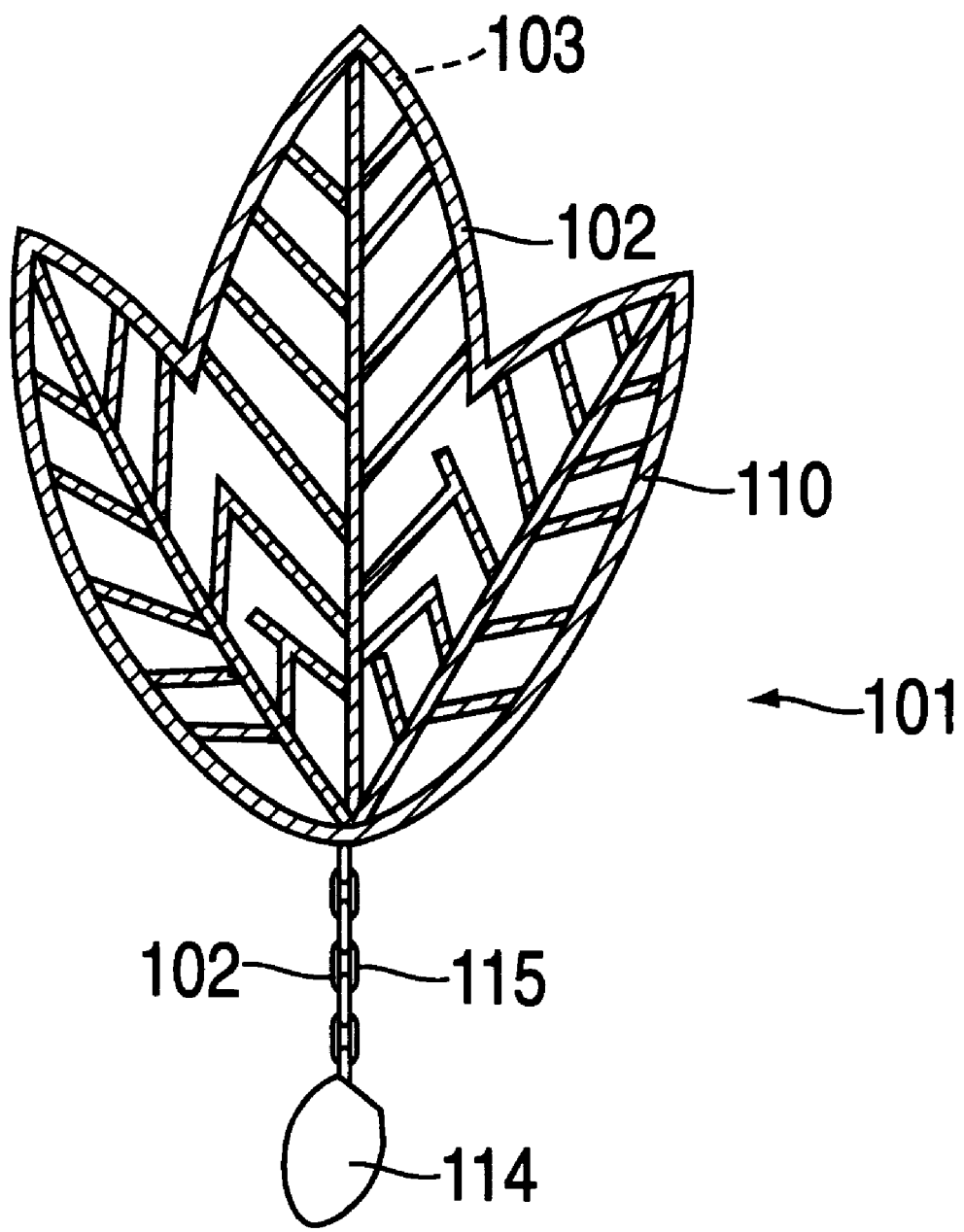
FIG. 15 illustrates the surface of a leaf-shaped earring with a magnet in accordance with the present invention.

In FIG. 15, conductive coating 102 is coated on the surface of the earring and insulating coating 103 is coated on the reverse side. Magnet 114 is attached below main part 110 by chain 115. In this case, conductive coating 102, which is coated on the surface of earrings 101, blocks permeation of electromagnetic waves. Also, insulating coating 103 which is coated on the reverse side of the earrings, absorb electromagnetic wave energy by causing dielectric polarization. Further, magnet 114 absorbs electromagnetic wave energy. Therefore, in the case where the earrings are coated with these coatings and/or the magnets attached, the electromagnetic waves from portable telephones, etc., are blocked by conductive coating 102, insulating coating 103, and magnet 114 before the waves permeate into the human body.

Any shape of earrings may be employed so long as electromagnetic waves are blocked as much as possible. Furthermore, the earrings can be formed bow-shaped and coil-shaped, wave-shaped, ring-shaped and in the shape of the veins of a leaf as illustrated in FIGS. 12–15.

Moreover, there is no restriction on the parts that can be coated with a conductive coating and/or with an insulating coating. For example, the conductive coating and the insulating coating can be coated on the reverse side of main parts 110 of the earrings as illustrated in FIGS. 11–13; and conductive coating can be coated on chain 115.

Furthermore, electromagnetic wave shield magnet 114 illustrated in FIGS. 13–15 can be affixed to earrings 101 in FIG. 12 to improve electromagnetic wave shield effect.

Clips for fitting earrings 101 to the ears can be fixed apart from the main part 110 in order to hang them from the ears. In this case, the conductive coating is coated on both sides of earrings 101.

The process for preparing a conductive coating and coating it on a conductive article, such as lens frame 14, is illustrated in FIG. 16. Broadly, a mixture comprising a conductive pigment, a liquid silicone and a hardener is prepared and applied to the article. Suitable liquid silicones include KMC-310 available from Shin-Etsu Chemicals Co. Ltd. and TSE221, TSE260 available from Toshiba Silicone Co. Ltd. The amount of silicone in the mix is about 50% to about 70% and, more preferably, about 55% to about 65%. Suitable conductive pigments include tin, titanium, and nickel powder, sericite, and mixtures thereof. The amount of conductive pigment in the mix is about 40 to about 70 parts and, more preferably, about 50 to about 60 parts by weight based on 100 parts silicone. Suitable hardeners include zinc, lead, and fatty acid cobalt esters. The amount of hardener in the mix is about 2 to about 15 parts and, more preferably, about 3 to about 12 parts by weight based on 100 parts silicone. As shown in FIG. 16, a mixture is formed by combining conductive pigment with a liquid silicon resin and a hardener; for example, 65% of a blend of a liquid silicon resin and hardener, and 35% of conductive pigments (a mixture of tin 14%, titanium 10%, nickel powder 8%, barium 2%, and sericite 0.5–1%). Next, kerosene and glycol were added to the mixture and the mixture was heated to about 60–70° C. Then, the mixture was fused for about 40 minutes at a temperature of about 60–70° C. Finally, the fused conductive coating was heated to about 120° C.–160° C. and sprayed or coated with a brush on a washed lens frame.

Transparent conductive coating 13 which is coated on the surface of the lens was, for example, prepared by combining 49%–28% tin and 1–2% sericite with 50%–70% epoxy resin. The mixture was then heated and the lens was coated by IP plating (plating at high temperature). That is, the conductive coating was vapor deposited on the surface of lens frames.

It has been found that a conductive coating (square-pilled portion of sectional area of 2.42 cm$^2$, length of 33.3 cm) which was prepared according to the above-stated processes gave a specific resistance of $18.9 \times 10^{-5}$. That is, this conductive coating showed high conductivity and had good electromagnetic shield effect.

Figure 17:
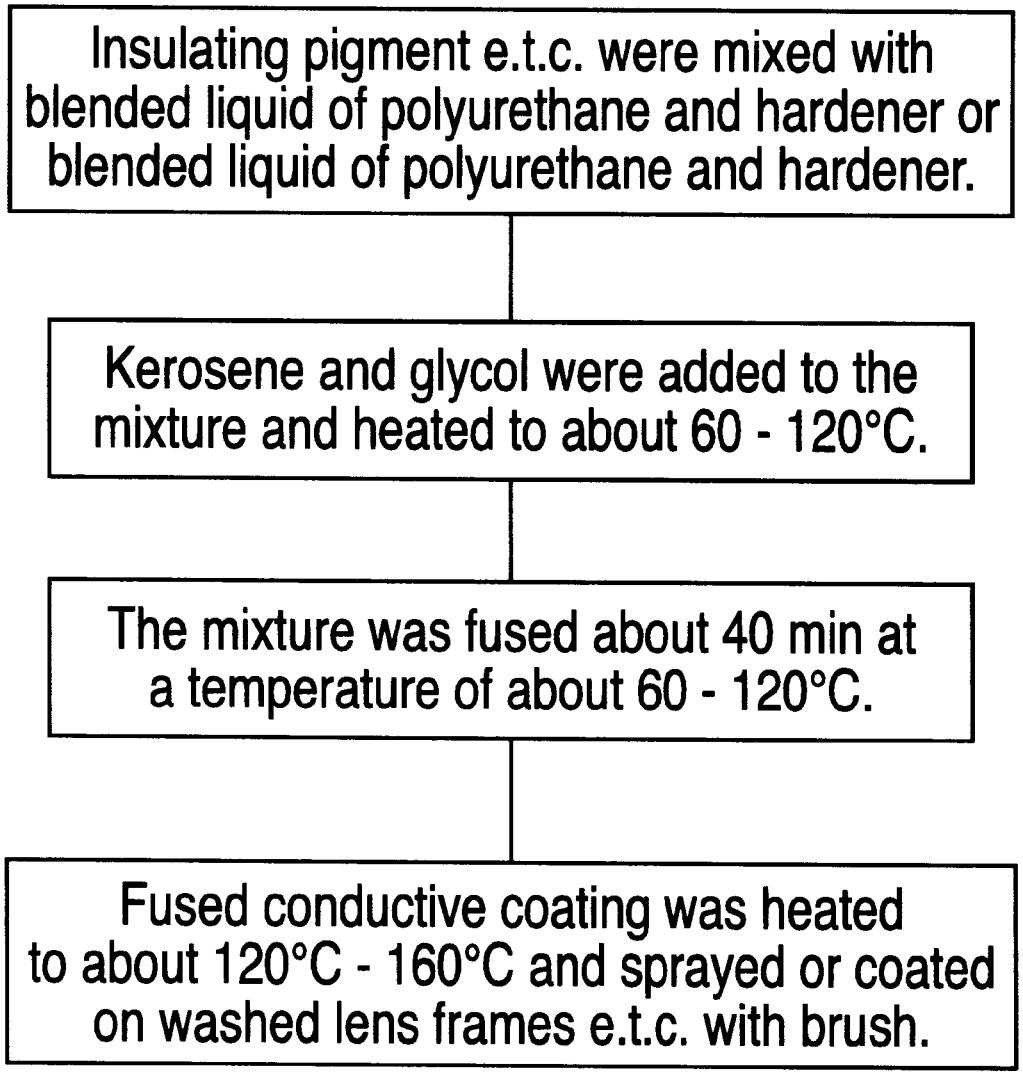
FIG. 17 illustrates a process for making an insulating coating and coating a lens in accordance with the present invention.
Figure 18A:
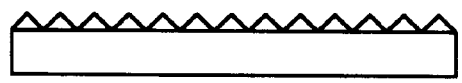
FIGS. 18(a)–18(d) illustrate examples of shape (a cross-sectional view) of the surface in the article having a conductive coating and an insulating coating thereon.
Figure 18B:
Figure 18C:
Figure 18D:
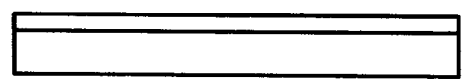

The process for preparing an insulating coating and coating it on a conductive article such as lens frame 14 is illustrated in FIG. 17. Broadly, a mixture comprising an insulating pigment, polyurethane and a hardener is prepared and then applied to the article. Suitable insulating pigments include lead powder, calcium phosphate, rubber sap, and mixtures thereof. The amount of insulating pigment in the mix is about 20 parts to about 100 parts and, more preferably, about 40 parts to about 100 parts based on 100 parts polyurethane. Suitable polyurethanes include 415 and 1204 available from Mitsubishi Chemical Corp. The amount of polyurethane in the mix is about 40% to about 82% and, more preferably, about 40% to about 70%. Suitable hardeners are aromatic diamine, polyhydric alcohol, and aliphatic diamine. The amount of hardener in the mix is about 2 parts to about 15 parts and, more preferably, about 3 parts to about 12 parts by weight based on 100 parts of polyurethane.

As shown in FIG. 17, insulating pigment, etc., were blended with liquid polyurethane and hardener. For example, 60% liquid polyurethane and hardener or blended liquid polyurethane and hardener was mixed with 40% insulating pigment (lead powder 10–11%), calcium phosphate 7%, rubber sap 7%, powdered pearl oyster shell 5%, varnish 4–5%, limestone 3–4%, alumina 1–2%, salicylic acid 0.5–1%, ultraviolet hardener, etc.). Next, kerosene and glycol were added and heated to about 60–120° C. Finally, the mixture was fused for about 40 minutes at a temperature of about 60–120° C. After that, the fused insulating coating was heated to about 120° C.–160° C. and sprayed or coated with a brush onto a washed lens frame.

The earrings which are coated with conductive coating and insulating coating can be made of metal or plastics. Also, earrings can be formed using materials which have been coated with these coatings beforehand.

As shown in FIG. 18, any form of coating (a), (b), (c), (a) can be employed. Also, other modifications besides these can be made.

Furthermore, electromagnetic wave shield magnets, conductive coating and insulating coating can be used by coating apparatus or devices that act as sources of stray electromagnetic waves. Furthermore machines such as medical electronic machines, etc. which receive undesirable electromagnetic waves can be coated with these coatings to shield the machines from stray electromagnetic waves.

In the present invention, an electromagnetic wave shield magnet is affixed to a conductive article, and electromagnetic wave energy is absorbed into this article by negative-ionization of said magnet. Furthermore, by an electromagnetic wave shield conductive coating and/or an electromagnetic wave shield insulating coating which are coated on the article in accordance with the present invention, effective absorption and/or reflection of electromagnetic wave energy is accomplished.

The electromagnetic wave shield magnets, conductive coatings and insulating coatings can be employed with:

eyeglasses, masks, aprons, earrings and other conventional wearing apparel which are worn in daily life;

parts of various kinds of apparatuses and devices which generate electromagnetic waves such as portable telephones, Braun tubes, microwave ovens, car engines, and motors of electric shavers and dryers by applying them to the conductive exterior or interior of the apparatus;

medical electronic machines by applying it to the exterior or interior or the device.

Consequently, the harmful influence caused by stray electromagnetic waves on the human body is inhibited and mis-measurement of medical electronic machines, etc. caused by undesirable electromagnetic waves is prevented.

As will be understood, any part or all of the conductive article can have the coatings of the present invention or have the magnet of the present invention affixed thereon. Moreover, the portion for the keeping paper battery can be coated with the conductive coating or insulating coating.

Electromagnetic waves are blocked by the coated portion and/or magnet when the eyeglasses, the masks and the earrings are worn in the presence of various kinds of electric machines such as personal computers, portable telephones, and microwave ovens. Therefore, the harmful influence caused by electromagnetic wave energy on the optic nerves, the periphery nerves such as the auditory nerves, the head and the central nerves can be reduced. If the eyeglasses, masks and earrings are worn jointly, electromagnetic waves can be blocked more widely. Still more, electromagnetic wave shield eyeglasses with a hearing aid can be used.

It will be understood that the claims are intended to cover all changes and modifications of the preferred embodiments of the invention herein chosen for the purpose of illustration which do not constitute a departure from the spirit and scope of the invention.

What is claimed is:

1. A method for making an electromagnetic wave shield magnet comprising:

treating a base magnet with an alkali aqueous solution containing as an essential ingredient therein chitosan, and recovering said base magnet from said solution.

2. The method of claim 1 wherein:

said solution is formed by combining water and an alkali at a temperature of about 40 to about 50° C. to obtain a pH of about 13 to about 14; adding enzyme and chitosan to said solution, said enzyme being added in an amount of about 10 g to about 20 g and said chitosan being added in an amount of about 20 g to about 40 g; and then raising the temperature of said solution to about 80 to about 90° C. and maintaining the temperature for about 30 minutes; and said treating comprises adding a magnet to said solution and maintaining said magnet in said solution for about 1 to about 2 days.

3. The method of claim 2 wherein said base magnet is selected from the group consisting of ferrite magnets, plastic bonded magnets, and rare earth magnets.

4. The method of claim 2 wherein said solution contains an alkali selected from the group consisting of sodium hydroxide (NaOH), potassium hydroxide (KOH), and calcium hydroxide ($Ca(CH)_2$).

5. The method of claim 2 wherein said enzyme is selected from the group consisting of adenosine triphosphate, endopeptidase, and deoxyribonuclease.

6. A method for making an electromagnetic wave shield article comprising:

treating a base magnet with an alkali aqueous solution containing as an essential ingredient therein chitosan;

recovering said base magnet from said solution;

applying a conductive coating to a base article; and affixing said base magnet recovered from said solution to said base article.

7. The method of claim 6 further comprising applying an insulating coating to said base article.

8. The method of claim 6 wherein said base article is a mask, eyeglasses, or earrings.

* * * * *